United States Patent [19]

Duffett et al.

[11] Patent Number: Plant 5,995

[45] Date of Patent: May 19, 1987

[54] CHRYSANTHEMUM PLANT NAMED TRIUMPH

[75] Inventors: William E. Duffett; Cornelis P. VandenBerg, both of Salinas, Calif.; Grace H. Mack, 108 Wahackme Rd., New Canaan, Conn. 06840

[73] Assignee: Grace H. Mack, New Canaan, Conn.

[21] Appl. No.: 767,518

[22] Filed: Aug. 20, 1985

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Triumph having flat capitulum form; decorative capitulum type; yellow-orange ray floret color; diameter across face of capitulum up to 8 cm.; short plant height; spreading branching pattern; average natural season flowering date of September 15 in the West Coast area; average flowering response period of seven weeks in photoperiodic controlled short day programs; and durable, uniform performance in Spring small pot flowering programs.

3 Drawing Figures

The present invention comprises a new and distinct cultivar of *Chrysanthemum morifolium,* Ramat., named Triumph.

Triumph is a product of a planned breeding program which had the objective of creating new Chrysanthemum cultivars with decorative capitulum type, short plant height, spreading branching pattern, durable inflorescence, six to seven week flowering response period, and orange ray floret color under outdoor natural season conditions.

Triumph, identified as 82M22001, was originated from a cross made by Grace H. Mack in a controlled breeding program in New Canaan, Conn. in the year 1981. The female parent, identified as M016, was an unnamed seedling. The male parent, identified as M5218, was an unnamed seedling bred from Revere, disclosed in U.S. Plant Pat. No. 4,005, crossed with M519, an unnamed seedling.

Triumph was discovered and selected as a flowering plant within the progeny of the stated cross by William E. Duffett in September 1982 in a controlled open area in Salinas, Calif.

The first act of asexual reproduction of Triumph was accomplished when vegetative cuttings were taken from the initial selection in February 1983 by Cornelis P. VandenBerg. Horticultural examination of selected units initiated September 1983 has demonstrated that the combination of characteristics as herein disclosed for Triumph are firmly fixed and are retained through successive generations of asexual reproduction.

Triumph has not been observed under all possible environmental conditions. The phenotype may vary significantly with variations in environment such as temperature, light intensity and day length. The observations, measurements and comparisons describe plants grown in a controlled open area in Salinas, Calif.

Rooted cuttings were established in soil and maintained outdoors under the natural temperature and day length prevailing during July through September. Single pinching was practiced with all branches and buds retained.

The following traits have been repeatedly observed and are determined to be basic characteristics of Triumph, which in combination distinguish this Chrysanthemum as a new and distinct cultivar:

(1) Flat capitulum form.
(2) Decorative capitulum type.
(3) Yellow-orange ray floret color.
(4) Diameter across face of capitulum up to 8 cm.
(5) Short plant height.
(6) Spreading branching pattern.
(7) Average natural season flowering date of September 15.
(8) Average flowering response of seven weeks in photoperiodic controlled flowering programs.
(9) Durable, uniform performance in Spring small pot flowering programs.

The accompanying photographic drawings show typical leaf and inflorescence characteristics of Triumph.

Sheet 1 is a color photograph of Triumph.

Sheet 2 is a black and white photograph of three views of the inflorescence of Triumph.

Sheet 3 is a black and white photograph showing the leaves of Triumph in three stages of growth (mature, intermediate and immature).

Of the many commercial cultivars known to the present inventors, the most similar in comparison to Triumph is the cultivar Revere, disclosed in U.S. Plant Pat. No. 4,005. Reference is made to attached Chart A which compares certain characteristics of Triumph to those same characteristics of Revere. Similar traits are type, form, capitulum diameter, permanence of form and color, and response. Triumph has a lighter ray floret color, earlier natural season flower date, shorter height and a larger, more spreading plant habit.

In the following description, color references are made to The Royal Horticultural Society Colour Chart. The color values were determined between 2:15 and 2:30 p.m. on Sept. 14, 1984 under 380 foot-candle light intensity at Salinas, Calif.

Classification:

*Botanical.*—*Chrysanthemum morifolium,* Ramat., cv Triumph.

*Commercial.*—Decorative spray pot mum and garden cultivar.

I. INFLORESCENCE

A. Capitulum:

*Form.*—Flat.

*Type.*—Decorative.

*Permanence.*—Approximately 14 days.

*Diameter across face.*—6 to 8 cm.

B. Corolla of ray florets:

*Color (general tonality from a distance of three meters).*—Yellow-orange.

*Color (upper surface).*—15C, 20A oxidizing to 14C.

*Color (under surface).*—20B, 20C.

*Shape.*—Broad; rounded tip. Clustered rays deepen the center color of the inflorescence.

C. Corolla of disc florets:

*Color (mature).*—3A.

*Color (immature).*—154C.

D. Reproductive organs:

*Androecium.*—Present disc florets; scant pollen.

*Gynoecium.*—Present both ray and disc florets.

II. PLANT

A. General appearance:

*Height.*—Short.

*Branching pattern.*—Spreading.

B. Foliage:

*Color (upper surface).*—147A.

*Color (under surface).*—147B.

*Shape.*—Shallow lobes. Moderate serration.

CHART A

COMPARISON OF TRIUMPH AND REVERE

| CULTIVAR | RAY FLORET COLOR | CAPITULUM FORM AND TYPE | AVERAGE NATURAL SEASON FLOWER DATE | PLANT HEIGHT |
|---|---|---|---|---|
| TRIUMPH | YELLOW-ORANGE | FLAT DECORATIVE | SEPTEMBER 15 | SHORT |
| REVERE | TWO TONE RED-BRONZE YELLOW-BRONZE | FLAT DECORATIVE | SEPTEMBER 20 | MEDIUM |

CHART A-continued

COMPARISON OF TRIUMPH AND REVERE

| CULTIVAR | BRANCHING PATTERN AND SPREAD | DIAMETER ACROSS FACE OF CAPITULUM | PERMANENCE OF FORM AND COLOR | CONTROLLED RESPONSE |
|---|---|---|---|---|
| TRIUMPH | SPREADING | 6 to 8 cm. | 14 DAYS | SEVEN WEEKS |
| REVERE | SEMI-SPREADING | 6 to 7 cm. | 14 DAYS | SEVEN WEEKS |

COMPARISONS MADE OF PLANTS GROWN UNDER NATURAL SEASON OUTDOOR CONDITIONS IN SALINAS, CALIFORNIA

We claim:

1. A new and distinct cultivar of *Chrysanthemum morifolium,* Ramat., named Triumph, as described and illustrated, and particularly characterized as to uniqueness by the combined characteristics of flat capitulum form, decorative capitulum type, yellow-orange ray floret color, diameter across face of capitulum up to 8 cm., short plant height, spreading branching pattern, average natural season flowering date of September 15 in the West Coast area, average flowering response period of seven weeks in photoperiodic controlled short day programs, and durable, uniform performance in Spring small pot flowering programs.

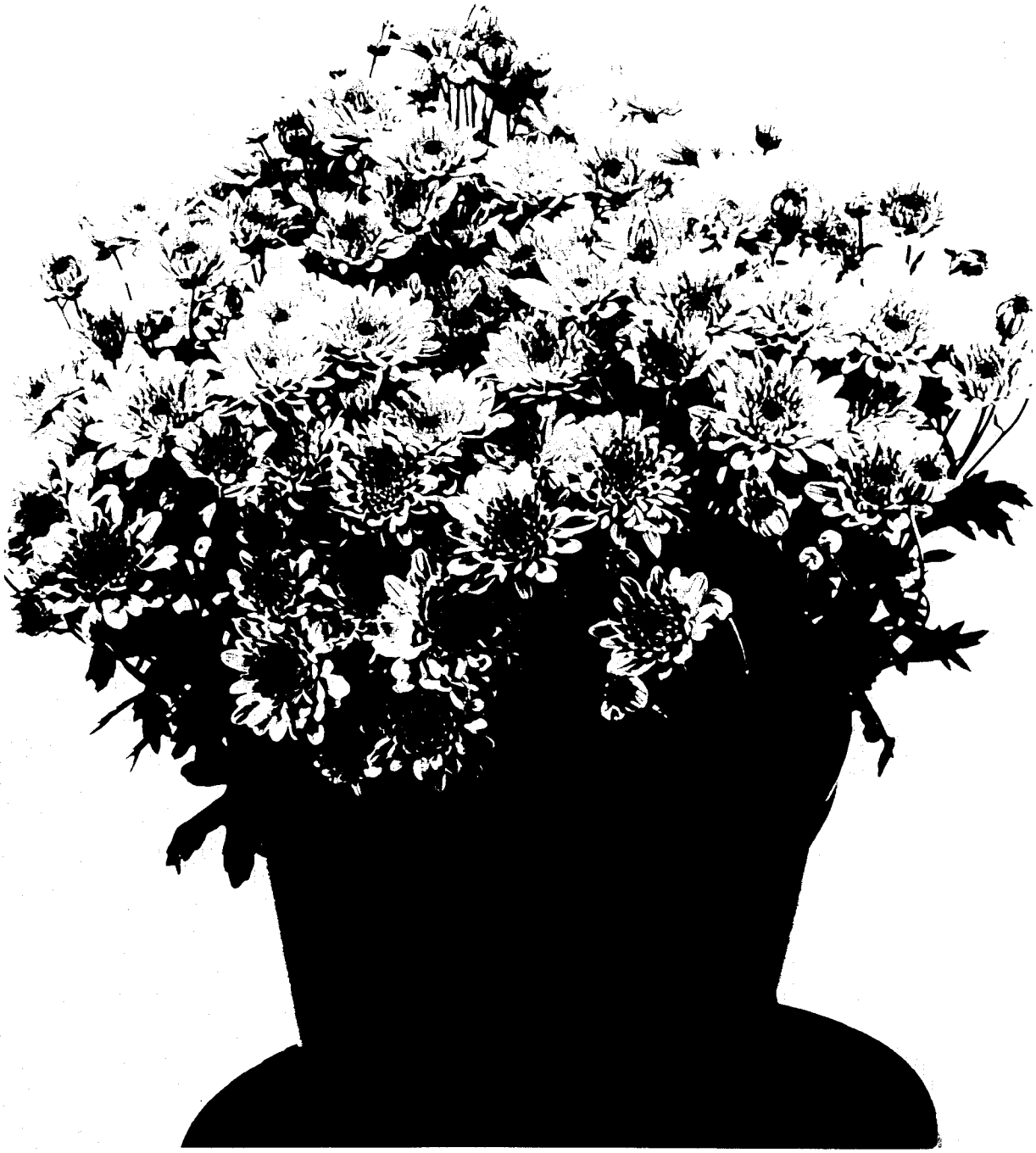

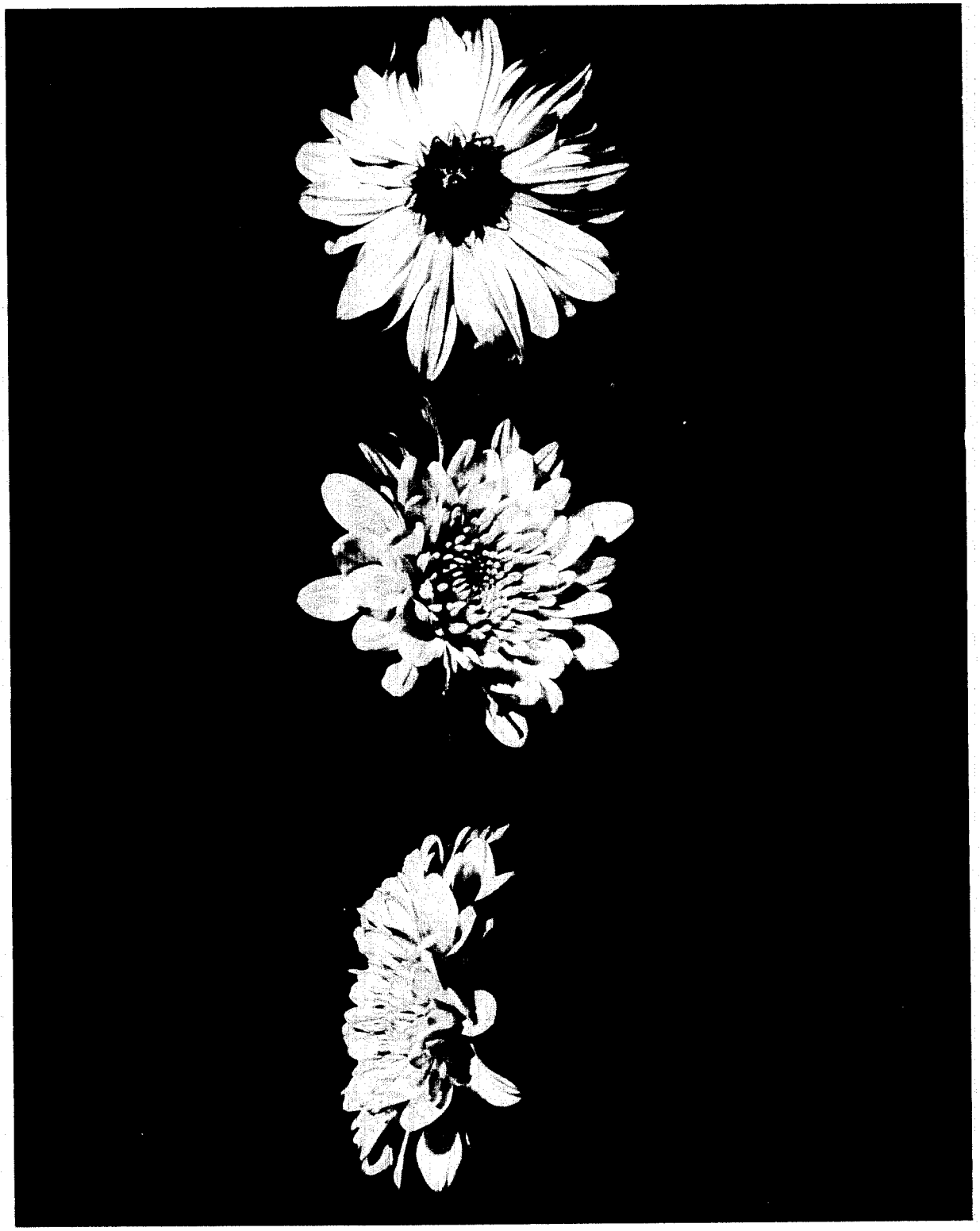

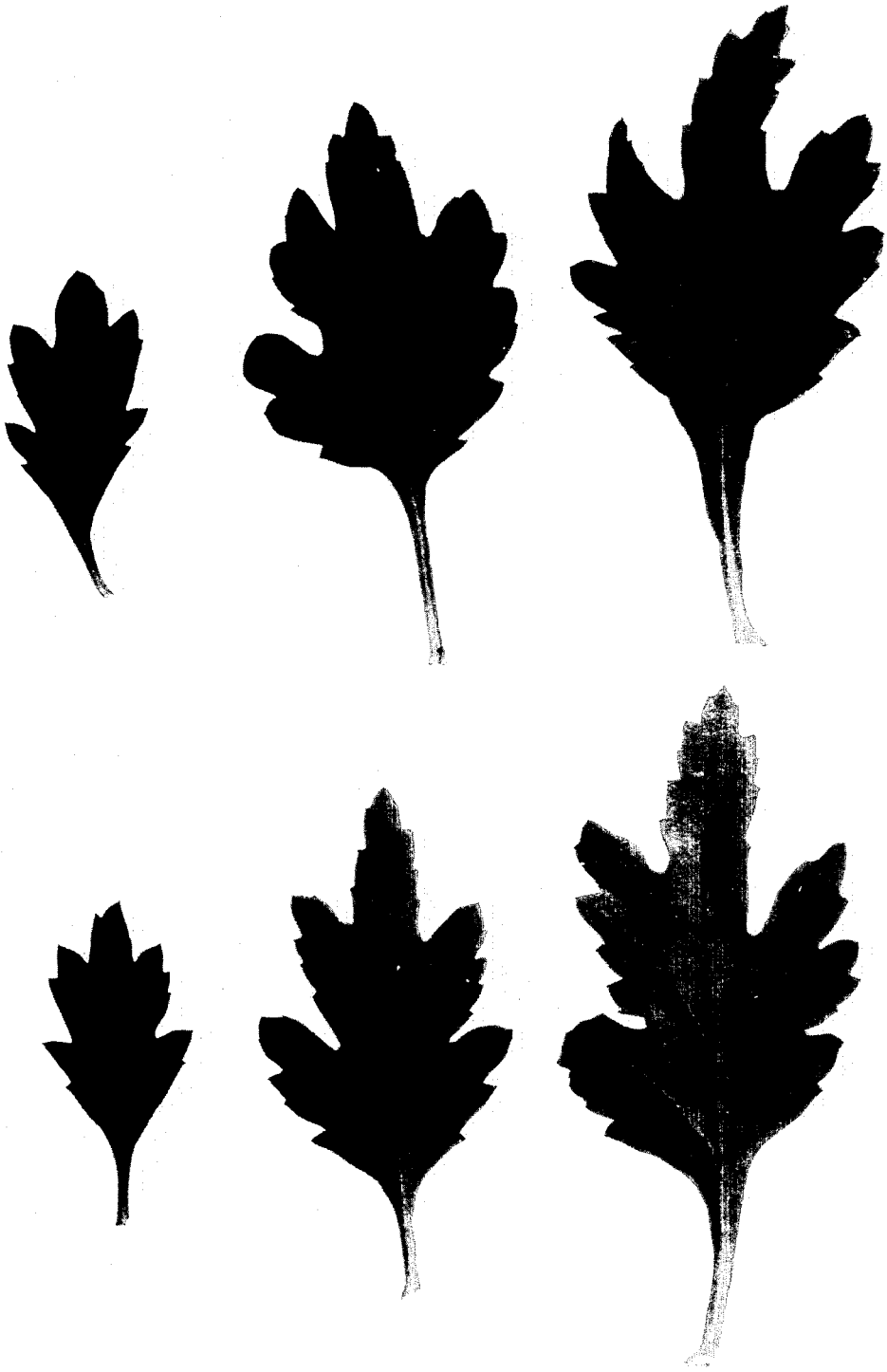

* * * * *